(12) United States Patent
Yam et al.

(10) Patent No.: US 7,755,826 B2
(45) Date of Patent: Jul. 13, 2010

(54) PHOTOCHROMIC DIARYLETHENE-CONTAINING COORDINATION COMPOUNDS AND THE PRODUCTION THEREOF

(75) Inventors: Vivian Wing-Wah Yam, Hong Kong (CN); Chi-Chiu Ko, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 421 days.

(21) Appl. No.: 11/598,131

(22) Filed: Nov. 13, 2006

(65) Prior Publication Data

US 2007/0057240 A1      Mar. 15, 2007

Related U.S. Application Data

(63) Continuation-in-part of application No. 10/883,677, filed on Jul. 6, 2004, now Pat. No. 7,355,775.

(60) Provisional application No. 60/484,668, filed on Jul. 7, 2003.

(51) Int. Cl.
*G02F 1/061* (2006.01)
*C09B 47/00* (2006.01)
*C07D 487/22* (2006.01)
*C07D 409/14* (2006.01)

(52) U.S. Cl. .................... 359/241; 540/121; 540/145; 549/59

(58) Field of Classification Search ................. 359/241; 540/121, 145; 549/59
See application file for complete search history.

(56) References Cited

U.S. PATENT DOCUMENTS

| | | | |
|---|---|---|---|
| 4,882,428 A * | 11/1989 | Irie | ............................. 540/121 |
| 5,175,079 A | 12/1992 | Van et al. | |
| 5,183,726 A | 2/1993 | Taniguchi et al. | |
| 5,443,940 A | 8/1995 | Tatezono et al. | |
| 5,622,812 A | 4/1997 | Tatezono et al. | |
| 6,359,150 B1 | 3/2002 | Fukudome et al. | |

FOREIGN PATENT DOCUMENTS

| | | |
|---|---|---|
| JP | 2-250877 | 10/1990 |
| JP | 3-14538 | 1/1991 |
| JP | 3-261762 | 11/1991 |
| JP | 3-261781 | 11/1991 |
| JP | 3-271286 | 12/1991 |
| JP | 4-282378 | 10/1992 |
| JP | 5-59025 | 3/1993 |
| JP | 5-222035 | 8/1993 |
| JP | 5-222036 | 8/1993 |
| JP | 5-222037 | 8/1993 |
| JP | 6-199846 | 7/1994 |
| JP | 8-245579 A | 9/1996 |
| JP | 10-45732 | 2/1998 |
| JP | 2000-72768 | 3/2000 |
| JP | 2000-344693 | 12/2000 |
| JP | 2001-48875 | 2/2001 |
| JP | 2002-226477 | 8/2002 |
| JP | 2002-265468 | 9/2002 |
| JP | 2002-285145 A | 10/2002 |
| JP | 2002-293784 | 10/2002 |

OTHER PUBLICATIONS

Medforth et al. "Unusual Aryl-Porphyrin Rotational Barriers in Peripherally Crowded Porphyrins" Inorganic Chemistry, 2003, vol. 42, pp. 2227-2241.*

Irie, Masahiro, et al.; "Thermally Irreversible Photochromic Systems, Reversible Photocyclization of Diarylethene Derivatives"; J. Org. Chem.; vol. 53; 1988; pp. 803-810.

Irie, Masahiro, et al.; "Thermally Irreversible Photochromic Systems, A Theoretical Study"; J. Org. Chem. ; vol. 53, 1988; pp. 6136-6138.

Irie, Masahiro; "Diarylethenes for Memories and Switches"; Chem. Rev.; vol. 100; 2000; pp. 1685-1716.

Ramdhanie et al. "Synthesis of the First Corrolazine: A New Member of the Porphyrinoid Family" Journal of the American Chemical Society 2001, Vo. 123, pp. 9447-9448.

* cited by examiner

*Primary Examiner*—Joseph R Kosack
(74) *Attorney, Agent, or Firm*—Robert D. Katz, Esq.; Cooper & Dunham LLP

(57) ABSTRACT

Diarylethene-containing ligands and their coordination compounds are described. The ligands display photochromism with UV excitation, while the coordination compounds display photochromism with both excitation in the UV region and excitation into lower energy absorption bands characteristic of the coordination compounds, through which the excitation wavelengths for the photocyclization can be extended from $\lambda \leq 340$ nm to wavelengths beyond 470 nm. Switching of the luminescence properties of the compounds has also been achieved through photochromic reactions.

8 Claims, 7 Drawing Sheets

(a) open form ⇌ 313 nm / 365, 540 nm ⇌ close form (b) open form ⇌ 313, 440 nm / 365, 540 nm ⇌ close form

PHOTOCHROMIC DIARYLETHENE-CONTAINING COORDINATION COMPOUNDS AND THE PRODUCTION THEREOF

CROSS REFERENCE TO RELATED APPLICATIONS

This application is a continuation-in-part of U.S. patent application Ser. No. 10/883,677 filed Jul. 6, 2004 now U.S. Pat. No. 7,355,755, which claims the benefit of U.S. provisional patent application No. 60/484,668 filed Jul. 7, 2003, the entirety of both disclosures being incorporated herein by reference.

FIELD OF THE INVENTION

This invention is related to the design and the photochromic behavior of novel photochromic ligands and their coordination compounds. The design of these photochromic ligands and their coordination compounds is based on the cis-diarylethene structure, which forms part of a mono- or poly-cyclic ring structure that contains one or more donor atom(s) or donor heteroatom(s) for coordination to an acceptor atom to form photochromic coordination compounds.

BACKGROUND OF THE INVENTION

Photochromism is defined as "a reversible transformation of a single chemical species being induced in one or both directions by absorption of electromagnetic radiation, with two states having different distinguishable absorption spectra." Thus, photochromic compounds are compounds that possess at least two isomeric forms which have different physical properties, such as absorption properties, refractivity, and the like, and can be transformed from one form to another by light excitations at prescribed wavelengths.

Photochromism has been intensively studied due to its potential use for optical recording and other optical functioning devices. To be practically used as optical recording materials, both isomeric forms must be thermally stable and possess excellent durability for reversible photochromic reactivity. Diarylethene is one class of photochromic compounds which possesses these properties, and therefore is a suitable class of compounds for the construction of optical functioning devices. The cis-configuration of both aryl groups in the diarylethenes studied is generally fixed by an upper cycloalkene structure, such as fluorinated alicyclic group, aromatic group, anhydride and maleimide group. Apart from the difference in absorption characteristics and the like between the two forms and their thermal stabilities, the availability of desirable excitation wavelengths that can be tuned and selected for the photochromic reactions also represents an important aspect in the design of materials for optical functioning devices. It has been shown that with the more π-conjugated upper cycloalkene structures, such as maleimide derivatives, in the diarylethene compounds, the photocyclization proceeded with lower energy excitation in the visible region.

Further information can be found in U.S. Pat. Nos. 5,175,079, 5,183,726, 5,443,940, 5,622,812, and 6,359,150; Japanese patents JP 2-250877, JP 3-014538, JP 3-261762, JP 3-261781, JP 3-271286, JP 4-282378, JP 5-059025, JP 5-222035, JP 5-222036, JP 5-222037, JP 6-199846, JP 10-045732, JP 2000-072768, JP 2000-344693, JP 2001-048875, JP 2002-226477, JP 2002-265468 and JP 2002-293784; and in Irie et al., "Thermally Irreversible Photochromic Systems. Reversible Photocyclization of Diarylethene Derivatives", Journal of Organic Chemistry, 1988, 53, 803-808, Irie et al., "Thermally Irreversible Photochromic Systems. A Theoretical Study", Journal of Organic Chemistry, 1988, 53, 6136-6138, and Irie, "Diarylethenes for Memories and Switches", Chemical Review, 2000, 100, 1685-1716. The photochromic compounds of this invention can be used in the same way as described in these references.

SUMMARY OF THE INVENTION

The present invention relates to the use of coordination compounds to perturb the properties of the diarylethenes in photochromic compounds. Described below is a report of the design, synthesis and studies of cis-diarylethene-containing ligands, with the upper cycloalkene being part of a mono- or poly-cyclic ring structure that contains one or more donor atom(s) or donor heteroatom(s), such as phenanthrolines, pyridines, imidazoles, pyrazoles, thiazoles, pyrroles, diazines, triazines, polypyridines, porphyrins and phthalocyanines and the like, for coordination compound formation.

The object of the present invention is to provide a new class of diarylethene-containing coordination compounds capable of displaying perturbed and sensitized photochromic properties. The invented photochromic compound is a coordination compound that contains a diarylethene with one or more donor atoms coordinated to an acceptor atom of the coordination compound. Any diarylethene in which the ethene group in a heterocyclic moiety, monocyclic or polycyclic, with any donor atom(s) capable of forming a coordination compound can be used in the present invention. There is no restriction on the nature of the aryl groups and they can be heteroaryl groups such as, for instance, thienyl groups. Likewise, any acceptor atoms which can be coordinated with the ethene-containing heterocyclic ligand moiety can be employed.

In a preferred form, the photochromic coordination compound is expressed by the following general formula (I):

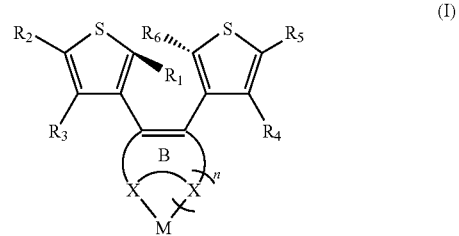

(I)

where unit B represents a mono- or poly-cyclic ring structure, such as phenanthroline, pyridine, imidazole, pyrazole, thiazole, pyrrole, diazine, triazine, polypyridine, porphyrin and phthalocyanine and the like, that contains one or more donor atom(s) X, such as carbon, or donor heteroatom(s) X, such as nitrogen, oxygen, sulfur, phosphorus, selenium, i.e., n is integer from 0 to 3, [M] represents the coordination unit containing an acceptor atom M, such as rhenium(I), zinc(II), ruthenium(II), osmium(II), rhodium(III), iridium(III), gold(III), gold(I), silver(I), copper(I), copper(II), platinum(II), palladium(II), iron(II), cobalt(III), chromium(III), cadmium(II), boron(III) and the like, $R_1$ and $R_6$ individually represent alkyl groups and alkoxy groups, and $R_2$ to $R_5$ individually represent atoms or groups selected from the group of hydrogen atom, halogen atom, hydroxyl group, alkyl group, alkoxy group, alkynyl group, cyano group, nitro group, alkylcarbonyl group, alkoxycarbonyl group, perfluoroalkyl group, aryl group, cycloalkyl group, arylcarbonyl group, aryloxycarbonyl group, mono- or dialkylaminocarbonyl group, alkylcarbonyloxy group, arylcarbonyloxy group, aryloxy group, alkoxycarbonyl group, aryloxycarbonyloxy group, and the like. In general, any alkyl or alkoxy group contains 1 to about 20 carbon atoms, any cycloalkyl group contains 3 to 8 carbon atoms, and any aryl group contains 6 to about 20 carbon atoms.

A non-limiting list of examples of diarylethene compounds containing a heterocyclic ethene-containing ligand moiety includes 5,6-dithienyl-1,10-phenanthroline, 2,3,7,8,12,13, 17,18-octathienyl-5,10,15,20-tetraphenyl porphyrin, 6,7-dithienyl-dipyrido[3,2-a:2',3'-c]phenazine and the like.

A non-limiting list of coordination units includes chlorotricarbonylrhenium(I), dithiolatozinc(II), dihaloplatinium(II), bipyridylplatinum(II), bis[bipyridyl]ruthenium(II), diphosphinocopper(I), bipyridylcopper(I) and the like.

One of the advantages of the formation of coordination compounds from their pure organic counterparts (free ligands) in this invention is the extension of the excitation wavelength for the photocyclization of the diarylethene moiety from $\lambda \leqq 340$ nm to lower energy, so that the photochromic forward reaction can proceed with visible light excitation by utilization of the low-energy absorptions characteristic of coordination compounds. In addition, the photochromic reactions can be utilized to switch the photoluminescence properties characteristic of the coordination compounds.

DESCRIPTION OF THE PREFERRED EMBODIMENTS

Example 1

Figure 1:
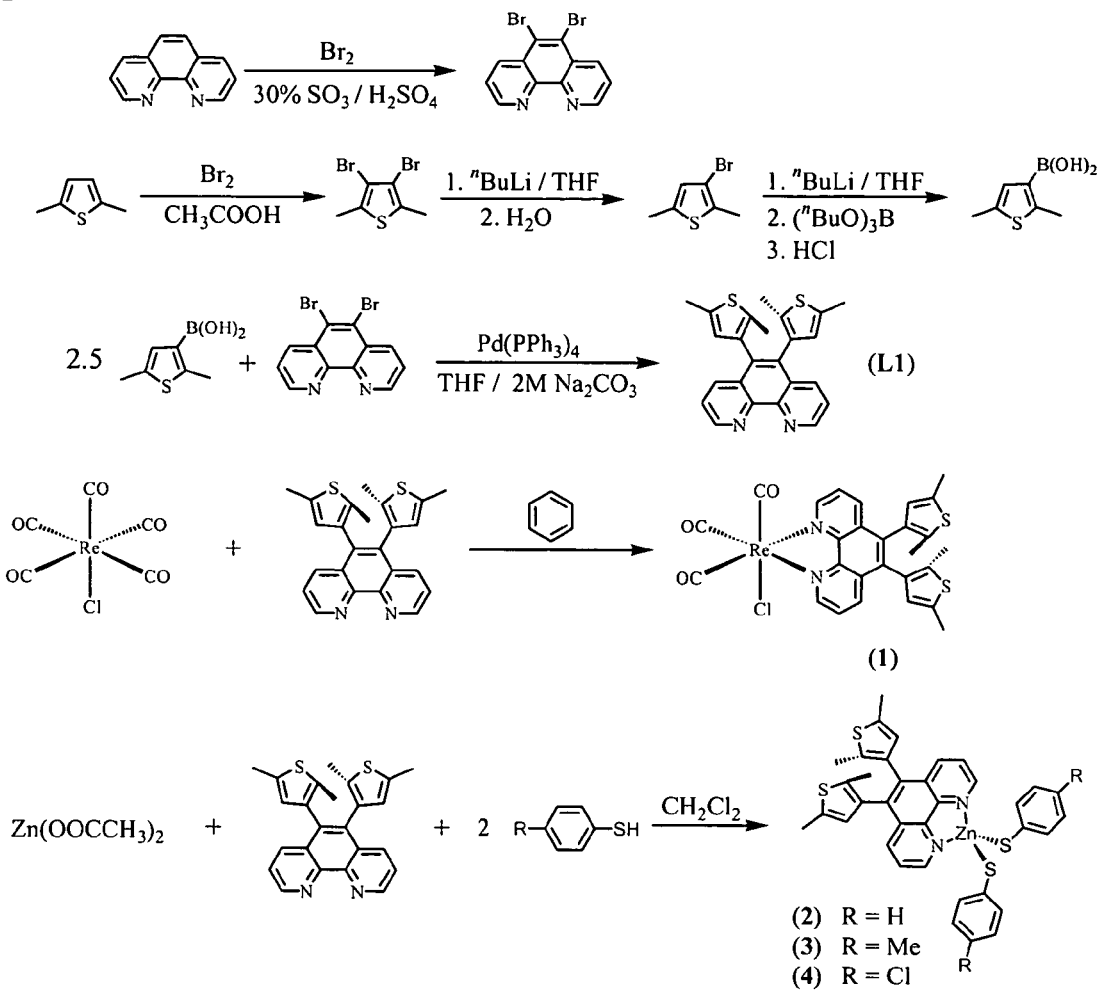
FIG. 1 shows a representative synthetic route for a diarylethene-containing ligand and its coordination compounds using 5,6-dithienyl-1,10-phenanthroline and its chlorotricarbonylrhenium(I) and dithiolatozinc(II) compounds as illustrative examples.
Figure 2:
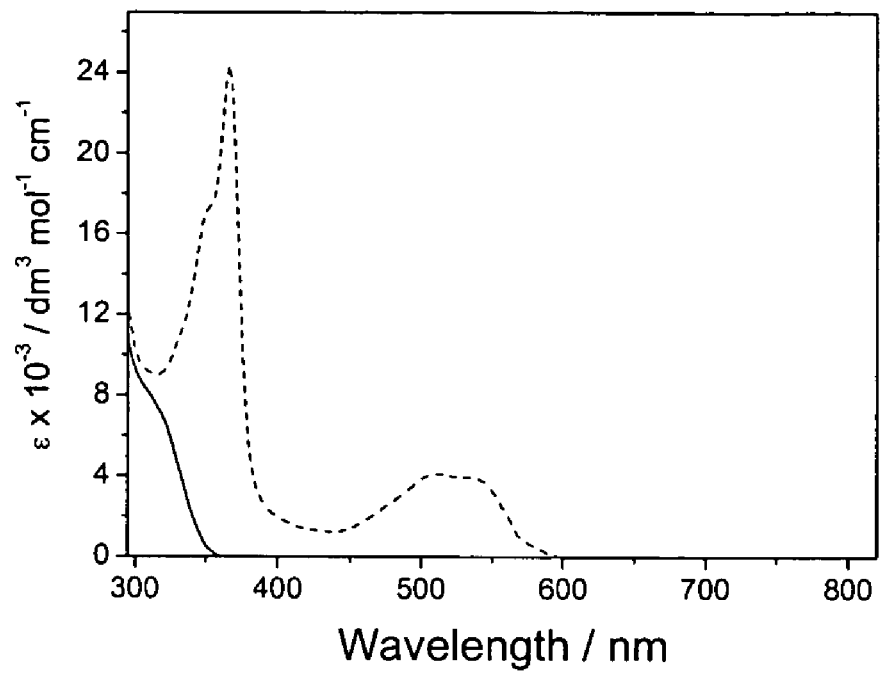
FIG. 2 shows the overlaid electronic absorption spectra of the open form (-) and the close form (- -) of a diarylethene-containing nitrogen donor ligand (L1).
Figure 3:
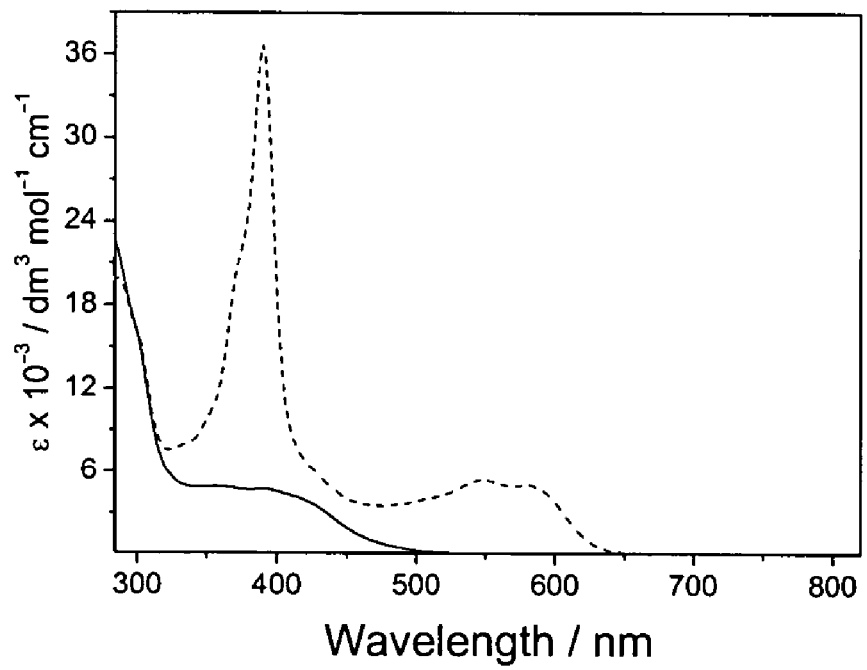
FIG. 3 shows the overlaid electronic absorption spectra of the open form (-) and the close form (- -) of a diarylethene-containing coordination compound (1).
Figure 4:
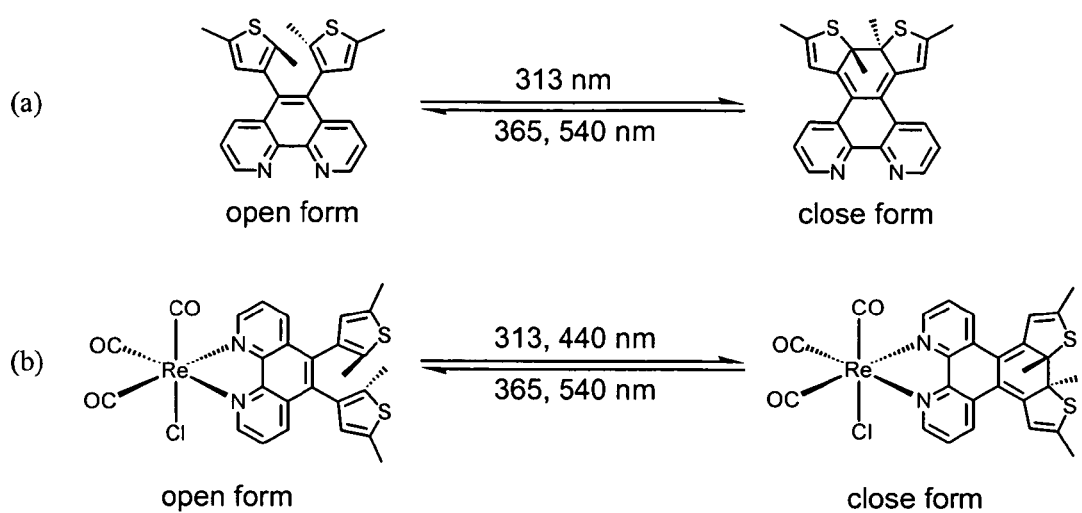
FIG. 4 shows the photochromic reactions of (a) a diarylethene-containing ligand and (b) its coordination compound using 5,6-dithienyl-1,10-phenanthroline and its chlorotricarbonylrhenium(I) compound as illustration.

The ligand (L1) is synthesized by the Suzuki cross-coupling reactions of 2.5 equivalents of 2,5-dimethyl-3-thienylboronic acid and 5,6-dibromo-1,10-phenanthroline in the presence of the palladium catalyst, $Pd(PPh_3)_4$, and sodium carbonate in a heterogeneous mixture of water and THF according to the synthetic route depicted in FIG. 1. Excitation of (L1) with 313 nm light resulted in the formation of the close form, corresponding to the photocyclization product. The overlaid electronic absorption spectra of the open and close forms of (L1) in benzene solution are shown in FIG. 2.

Upon coordination to a chlorotricarbonylrhenium(I) complex, the open form of the corresponding complex (1) undergoes photocyclization with the excitation of both the intraligand absorptions at $\lambda \leqq 340$ nm and the metal-to-ligand charge transfer (MLCT) absorption characteristic of this coordination compound up to $\lambda \leqq 480$ nm. The electronic absorption data of (L1) and complex (1) are summarized in Table 1. The close forms of these compounds are found to undergo thermal backward reactions. The half-lives of the close forms have been determined and summarized in Table 2. The quantum yields for both photocyclization and photocycloreversion of (L1) and its rhenium complex (1) are summarized in Table 3.

TABLE 1

| Compound | Configuration | Absorption (in benzene) $\lambda_{abs}$/nm ($\epsilon$/dm$^3$ mol$^{-1}$ cm$^{-1}$) |
|---|---|---|
| (L1) | Open form | 304 (8670) |
| (L1) | Close form | 366 (24340), 510 (4050), 540 (3860) |
| (1) | Open form | 338 (4930), 396(4690) |
| (1) | Close form | 390 (36670), 546 (5390), 580 (5050) |

TABLE 2

| Compound | Half-lives ($t_{1/2}$) at 20° C. | Half-lives ($t_{1/2}$) at 60° C. |
|---|---|---|
| (L1) | 143 hours | 222 mins |
| (1) | 77.7 hours | 79.3 mins |

TABLE 3

| | Photochemical Quantum Yield/$\phi$ | | | |
|---|---|---|---|---|
| | Photocyclization[a] | | Photo-cycloreversion | |
| Compound | $\phi$313 | $\phi$440 | $\phi$365 | $\phi$510 |
| (L1) | 0.486 | 0 | 0.123 | 0.029 |
| (1) | 0.552 | 0.648 | 0.028 | 0.009 |

Figure 5:
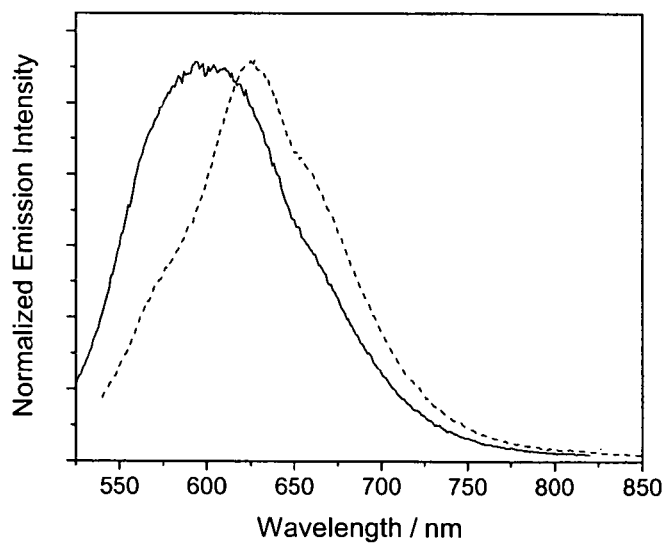
FIG. 5 shows the overlaid corrected emission spectra of the open form (-) and the close form (- -) of (1) in benzene solution at 298 K.
Figure 6:
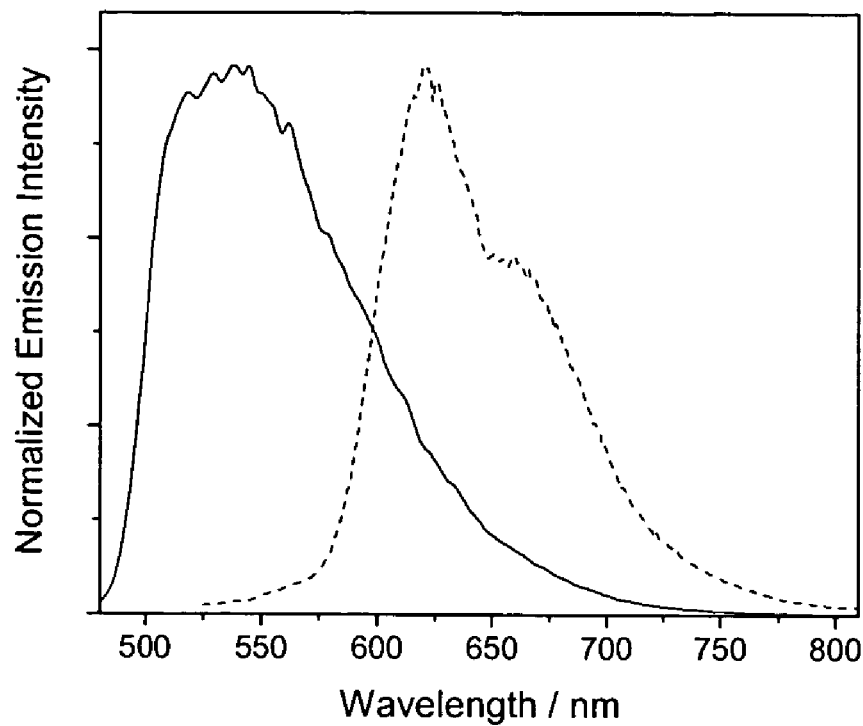
FIG. 6 shows the overlaid corrected emission spectra of the open form (-) and the close form (- -) of (1) in EtOH-MeOH (4:1 v/v) glass at 77 K.

[a]Values reported are corrected to the ratio of the photochromic active conformation, i.e. with respect to the anti-parallel configuration The photoluminescence properties of both the open and close forms were measured. FIGS. 5 and 6 display the overlaid emission spectra of the open form and the close form of complex (1) in benzene at 298 K and in EtOH-MeOH glass (4:1 v/v) at 77 K. The emission of complex (1) was found to change from metal-to-ligand charge transfer (MLCT) phosphorescence to ligand-centered (LC) phosphorescence upon photocyclization of the open form to the close form. These demonstrate the change of emission properties upon photochromic reactions. Table 4 summarized the emission data of ligand (L1) and complex (1).

TABLE 4

| Compound | Medium (T/K) | Emission $\lambda_{em}{}^a$/nm ($\tau_o$/µs) | |
|---|---|---|---|
| | | Open form | Close form |
| (L1) | Benzene (298) | 383 (<0.1) | 644 (<0.1) |
| | Glass$^b$ (77) | —$^c$ | 577 (5.2) |
| (1) | Benzene (298) | 595 (0.26) | 626 (<0.1) |
| | Glass$^b$ (77) | 535 (7.2) | 620 (6.4) |

$^a$Excitation wavelength at ca. 355 nm. Emission maxima are corrected values.
$^b$EtOH—MeOH (4:1, v/v)
$^c$Non-emissive Example 2

Figure 7:
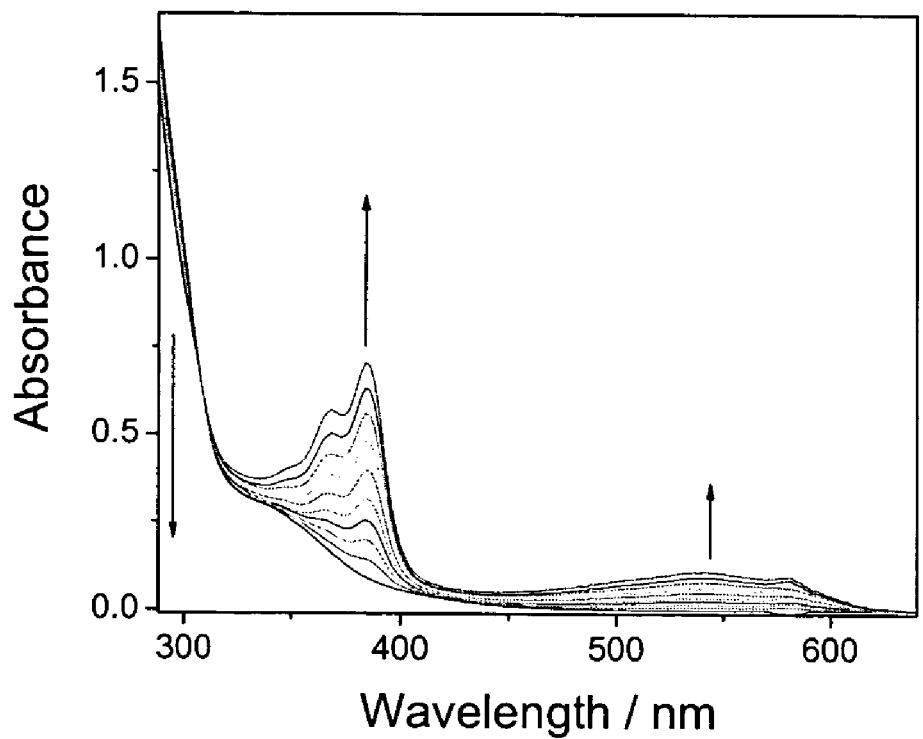
FIG. 7 shows the absorption spectral changes of complex (4) in benzene upon excitation at $\lambda$=300 nm.

Upon coordination of (L1) to a dithiolatozinc(II) complex, the open forms of the corresponding complexes (2), (3) and (4) undergo photocyclization with excitation at $\lambda \leq 340$ nm. FIG. 7 shows the absorption spectral changes of complex (4) upon excitation at $\lambda = 300$ nm. The electronic absorption maxima of both the open and the close forms of complexes (2), (3) and (4) are summarized in Table 5.

TABLE 5

| Complex | Configuration | Absorption maximum (in benzene) $\lambda_{abs}$/nm |
|---|---|---|
| (2) | Open form | 302, 326, 378 |
| (2) | Close form | 366, 382, 536, 576 |
| (3) | Open form | 302, 326, 382 |
| (3) | Close form | 366, 382, 538 |
| (4) | Open form | 302, 336, 396 |
| (4) | Close form | 366, 384, 542, 584 |

Those skilled in the art will recognize that various changes and modifications can be made in the invention without departing from the spirit and scope thereof. The various embodiments described were for the purpose of further illustrating the invention and were not intended to limit it.

Example 3

Figure 8:
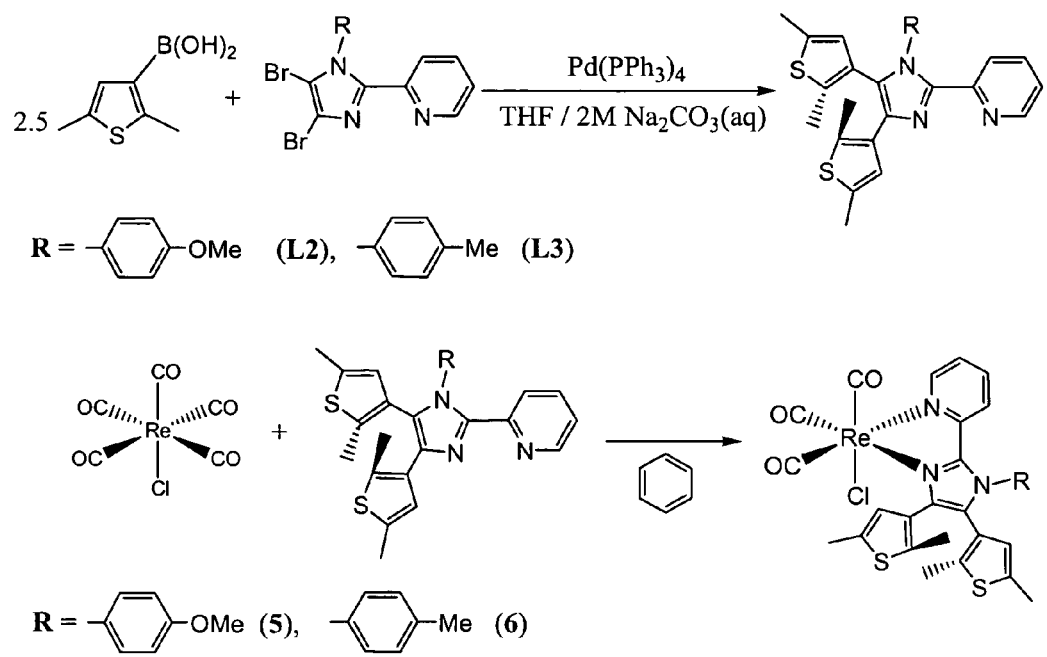
FIG. 8 shows a representative synthetic route for diarylethene-containing ligands and their coordination compounds using 1-(aryl)-bis-(2,5-dimethyl-3-thienyl)-2-(2-pyridyl)imidazoles and their chlorotricarbonylrhenium(I) compounds as illustrative examples.

The ligands, 1-(4-methoxyphenyl)-bis-(2,5-dimethyl-3-thienyl)-2-(2-pyridyl)imidazole (L2) and 1-(4-methylphenyl)-bis-(2,5-dimethyl-3-thienyl)-2-(2-pyridyl)imidazole (L3), are synthesized by Suzuki cross-coupling reactions of 2.5 equivalents of 2,5-dimethyl-3-thienylboronic acid and 1-aryl-4,5-dibromo-2-(2-pyridyl)imidazole in the presence of the palladium catalyst, Pd(PPh$_3$)$_4$, and sodium carbonate in a heterogeneous mixture of water and THF according to the procedure similar to that of (L1) as depicted in FIG. 8. Excitation of (L2) and (L3) with 313 nm light resulted in the formation of the close form, corresponding to the photocyclization product.

Figure 9:
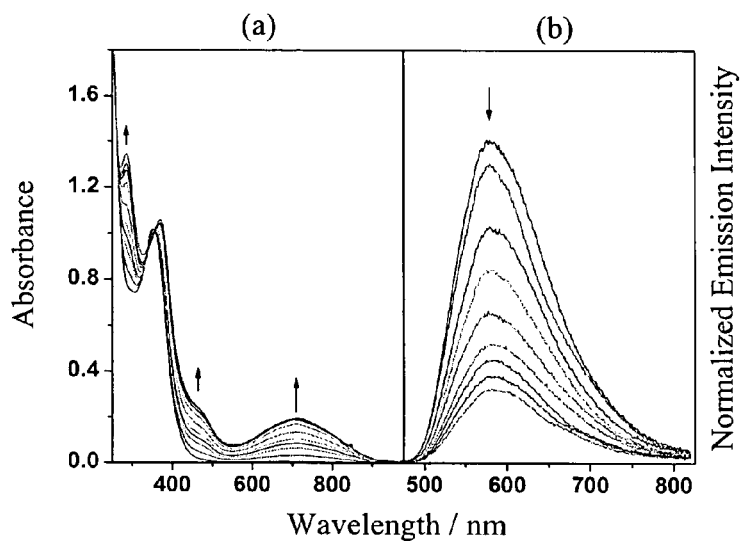
FIG. 9 shows (a) the absorption and (b) emission spectral changes of complex (6) in degassed chloroform solution ($7.16 \times 10^{-5}$ M) upon MLCT excitation at $\lambda$=410 nm.

Similar to ligand (L1), upon coordination of (L2) and (L3) to chlorotricarbonylrhenium(I) complex, the open form of the corresponding complexes (5) and (6) undergo photocyclization with the excitation of both the intraligand absorptions at $\lambda \leq 370$ nm and the metal-to-ligand charge transfer (MLCT) absorption characteristic of this coordination compound up to $\lambda \leq 470$ nm. The electronic absorption data of ligands (L2)-(L3) and complexes (5)-(6) are summarized in Table 6. Apart from the change in the absorption properties, the emissions of all the complexes were also found to drop significantly upon conversion to the close form. These further illustrate the change of emission properties upon photochromic reactions. The representative emission and electronic absorption spectral changes of the open form in chloroform solution upon photo-irradiation are shown in FIG. 9.

TABLE 6

| Compound | Configuration | Absorption maximum (in chloroform) $\lambda_{abs}$/nm |
|---|---|---|
| (L2) | Open form | 320 |
| (L2) | Close form | 330, 425, 586 |
| (L3) | Open form | 319 |
| (L3) | Close form | 334, 410, 576 |
| (5) | Open form | 352, 425sh |
| (5) | Close form | 284, 374, 475, 712 |
| (6) | Open form | 353, 425sh |
| (6) | Close form | 286, 376, 480, 713 |

Example 4

Figure 10:
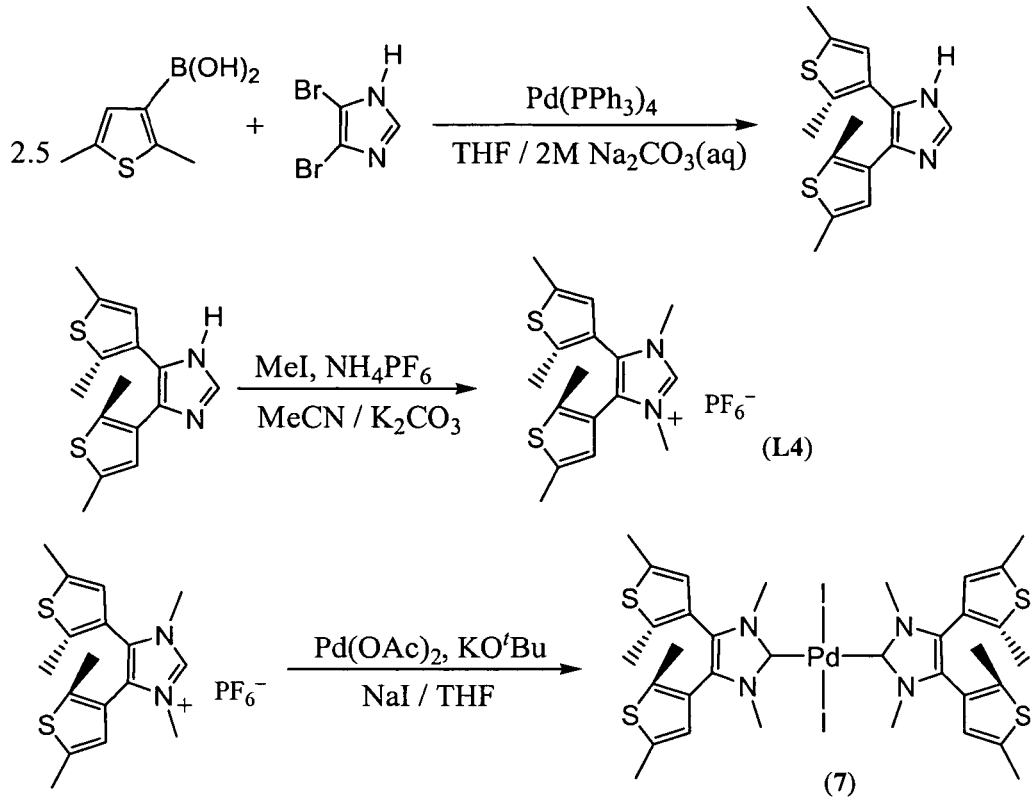
FIG. 10 shows a representative synthetic route for a diarylethene-containing ligand and its coordination compounds using 1,3-dimethyl-4,5-bis-(2,5-dimethyl-3-thienyl)-imidazolium hexafluorophosphate and its diiodopalladium(II) compounds as illustrative examples.

The ligand, 1,3-dimethyl-4,5-bis-(2,5-dimethyl-3-thienyl)-imidazolium hexafluorophosphate (L4), is synthesized by the methylation of 4,5-bis-(2,5-dimethyl-3-thienyl)-1H-imidazole, which is also prepared using Suzuki cross-coupling reactions of 2.5 equivalents of 2,5-dimethyl-3-thienylboronic acid and 4,5-dibromo-1H-imidazole in the presence of the palladium catalyst, Pd(PPh$_3$)$_4$, and sodium carbonate in a heterogeneous mixture of water and THF according to the procedure similar to that of (L1), as depicted in FIG. 10. Excitation of the ligand with $\lambda \leq 290$ nm light resulted in the formation of the close form, corresponding to the photocyclization product.

Figure 11:
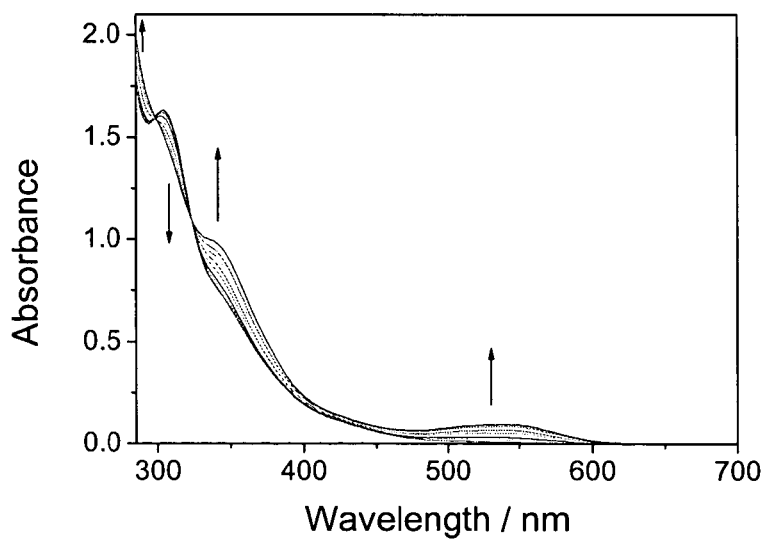
FIG. 11 shows the absorption spectral changes of complex (7) in dichloromethane solution ($1.21 \times 10^{-4}$ M) upon excitation at $\lambda$=310 nm.

Upon coordination to palladium(II) iodide to form the bis[1,3-dimethyl-4,5-bis(2,5-dimethyl-3-thienyl)-imidazol-2-ylidene]diiodopalladium(II) complex, the open form of the corresponding complex (7) undergoes photocyclization with the excitation of both the intraligand absorptions at $\lambda \leq 290$ nm and the absorption characteristic of this coordination compound up to $\lambda \leq 320$ nm. The electronic absorption data of ligand (L4) and complex (7) are summarized in Table 7. The representative electronic absorption spectral changes of complex (7) in dichloromethane solution upon photo-irradiation are shown in FIG. 11.

TABLE 7

| Compound | Configuration | Absorption maximum (in dichloromethane) $\lambda_{abs}$/nm |
|---|---|---|
| (L4) | Open form | 235 |
| (L4) | Close form | 350, 580 |
| (7) | Open form | 240, 305 |
| (7) | Close form | 345, 540 |

Example 5

Figure 12:
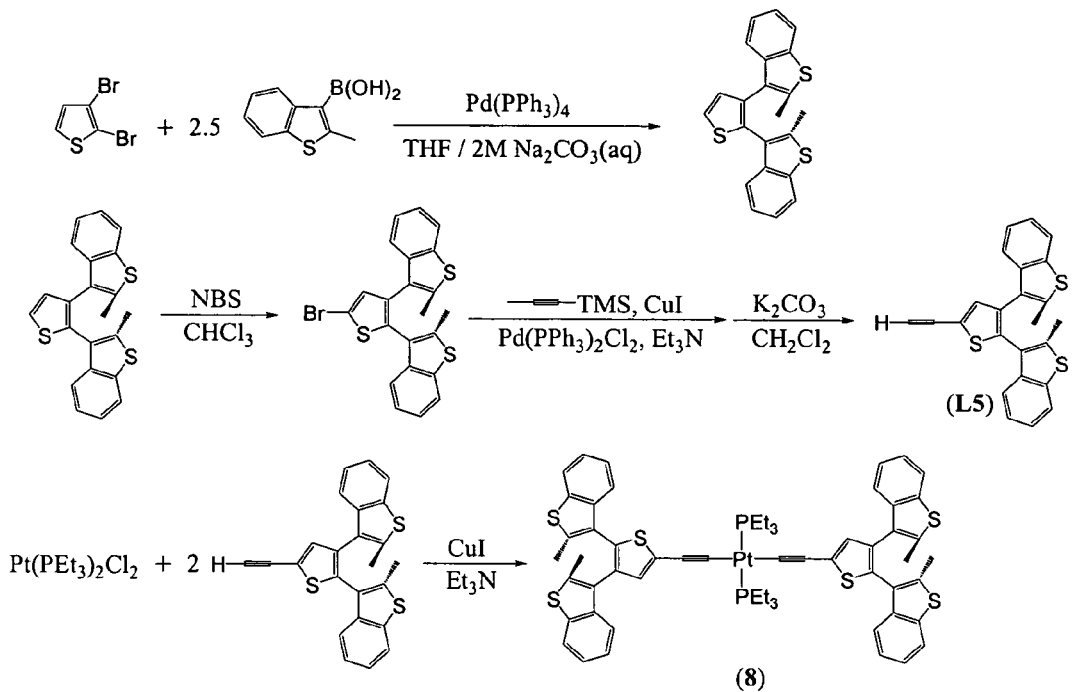
FIG. 12 shows a representative synthetic route for diarylethene-containing ligand and its coordination compounds using 5-ethynyl-2,3-bis-(2-methyl-3-benzo[3,2-b]thienyl)thiophene and its bis(triethylphosphine)platinum(II) compounds as illustrative examples.

5-Trimethylsilylethynyl-2,3-bis-(2-methyl-3-benzo[3,2-b]thienyl)thiophene is synthesized by the Sonogashira coupling reaction of trimethylsilylacetylene and the bromo-derivative of 2,3-bis-(2-methyl-3-benzo[3,2-b]thienyl)thiophene, which is also prepared from the Suzuki cross-coupling reaction of 2.5 equivalents of 2-methyl-3-benzo[3,2-b]thienylboronic acid and 2,3-dibromothiophene in the presence of the palladium catalyst, Pd(PPh$_3$)$_4$, and sodium carbonate in a heterogeneous mixture of water and THF according to the procedure similar to that of (L1). Subsequent deprotection of the trimethylsilyl group using potassium carbonate in dichloromethane solution gives the target ligand ethynyl-2,3-bis-(2-methyl-3-benzo[3,2-b]thienyl)thiophene (L5). The synthetic route is shown in FIG. 12. Excitation of the ligand with $\lambda \leq 352$ nm light resulted in the formation of the close form, corresponding to the photocyclization product.

Figure 13:
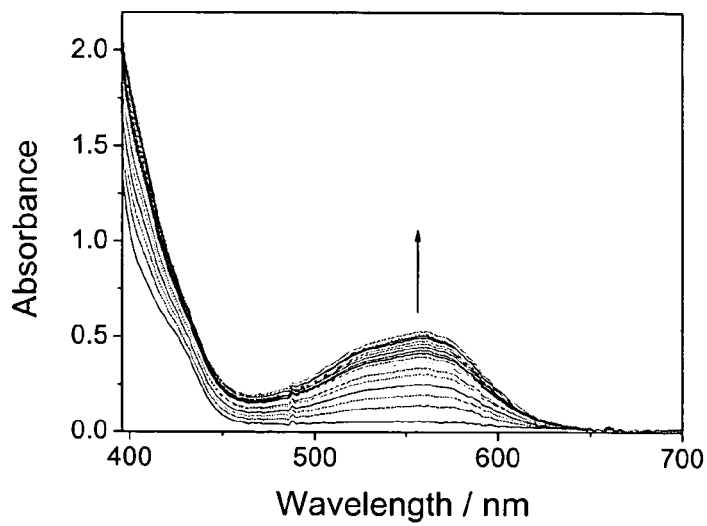
FIG. 13 shows the absorption spectral changes of complex (8) in dichloromethane solution ($3.10 \times 10^{-4}$ M) upon excitation at $\lambda$=400 nm.

Upon reaction with dichlorobis(triethylphosphine)platinum(II), the open form of the corresponding complex (8) undergoes photocyclization with the excitation up to λ≦430 nm. The electronic absorption data of ligand (L5) and complex (8) are summarized in Table 8. The representative electronic absorption spectral changes of complex (8) in dichloromethane solution upon photo-irradiation are shown in FIG. 13.

TABLE 8

| Compound | Configuration | Absorption maximum (in dichloromethane) $\lambda_{abs}$/nm |
| --- | --- | --- |
| (L5) | Open form | 260, 294, 304, 314sh |
| (L5) | Close form | 300, 382, 554 |
| (8) | Open form | 260sh, 296, 304, 318sh, 384 |
| (8) | Close form | 372, 560 |

What is claimed is:

1. The photochromic compound which is a diarylethene-containing coordination compound in which the diarylethene contains part of a monocyclic or polycyclic structure with one or more donor atoms or heteroatoms coordinated to a coordination unit [M], which contains an acceptor atom, M, expressed by the general formula (I):

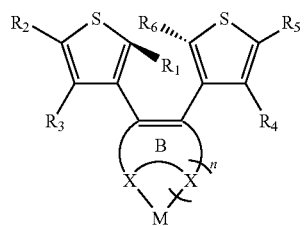

(I)

where unit B is porphyrin or azaporphyrin, each donor atom X is nitrogen, n is 3, [M] represents a coordination unit containing an acceptor atom M wherein the acceptor atom M is rhenium(I), zinc(II), ruthenium(II), osmium(II), rhodium(III), iridium(III), gold(III), gold(I), silver(I), copper(I), copper(II), platinum(II), palladium(II), iron(II), cobalt(III), chromium(III), cadmium(II), or boron(III), $R_1$ and $R_6$ individually represent an alkyl group or an alkoxy group, and $R_2$ to $R_5$ individually represent atoms or groups selected from hydrogen atom, halogen atom, hydroxyl group, alkyl group, alkoxy group, alkynyl group, cyano group, nitro group, alkylcarbonyl group, alkoxycarbonyl group, perfluoroalkyl group, aryl group, cycloalkyl group, arylcarbonyl group, aryloxycarbonyl group, mono- or dialkylaminocarbonyl group, alkylcarbonyloxy group, arylcarbonyloxy group, aryloxy group, alkoxycarbonyl group, and aryloxycarbonyloxy group.

2. The photochromic compound in accordance with claim 1, wherein unit B is a porphyrin.

3. The photochromic compound in accordance with claim 2, wherein $R_1$ and $R_6$ represent methyl groups, and $R_3$ and $R_4$ represent hydrogen atoms.

4. The photochromic compound in accordance with claim 2, wherein $R_2$ and $R_5$ represent hydrogen atoms.

5. The photochromic compound in accordance with claim 2, wherein $R_2$ and $R_5$ represent methyl groups.

6. The photochromic compound in accordance with claim 2, wherein $R_2$ end $R_5$ represent bromine atoms.

7. The photochromic compound in accordance with claim 2, wherein M represents zinc(II).

8. The photochromic compound in accordance with claim 2, wherein M represents platinum (II).

* * * * *